(12) United States Patent
Kraus-Guentner et al.

(10) Patent No.: US 9,008,266 B2
(45) Date of Patent: Apr. 14, 2015

(54) DEVICE FOR DETERMINING THE QUALITY OF ORTHOGONALLY PRETENSIONED LEATHER

(75) Inventors: Georg Kraus-Guentner, Weiz (AT); Elisabeth Kraus-Guentner, Weiz (AT)

(73) Assignee: Wollsdorp Leder Schmidt & Co. Ges.m.b.H, Weiz (AT)

( * ) Notice: Subject to any disclaimer, the term of this patent is extended or adjusted under 35 U.S.C. 154(b) by 370 days.

(21) Appl. No.: 13/522,694

(22) PCT Filed: Dec. 23, 2010

(86) PCT No.: PCT/EP2010/070654
§ 371 (c)(1),
(2), (4) Date: Jul. 17, 2012

(87) PCT Pub. No.: WO2011/085935
PCT Pub. Date: Jul. 21, 2011

(65) Prior Publication Data
US 2012/0307969 A1  Dec. 6, 2012

(30) Foreign Application Priority Data
Jan. 18, 2010 (AT) .................................. A 57/2010

(51) Int. Cl.
*G01N 21/89* (2006.01)
*G01N 33/44* (2006.01)
(Continued)

(52) U.S. Cl.
CPC .............. *G01N 33/447* (2013.01); *C14B 17/16* (2013.01); *G01N 23/043* (2013.01); *G01N 2223/612* (2013.01); *G01N 2223/646* (2013.01)

(58) Field of Classification Search
CPC ..... G01N 23/00; G01N 23/02; G01N 23/083; G01N 23/16; G01N 23/18
USPC .............................................. 378/51, 58, 208
See application file for complete search history.

(56) References Cited

U.S. PATENT DOCUMENTS 8,238,635 B2 * 8/2012 Can et al. ...................... 382/131
2004/0066890 A1 * 4/2004 Dalmijn et al. ................. 378/57

FOREIGN PATENT DOCUMENTS

DE  25 52 966         6/1977
DE  4 216 469 A1    11/1993
(Continued)

OTHER PUBLICATIONS

International Preliminary Report on Patentability and Written Opinion, Int'l Patent Appln. No. PCT/EP2010/070654, Aug. 7, 2012.

*Primary Examiner* — Michael Maskell
(74) *Attorney, Agent, or Firm* — Fitzpatrick, Cella, Harper & Scinto

(57) ABSTRACT

In a testing device (10) for determining the quality of leather (9) in the production of leather, wherein the testing device (10) is formed for examining a quality category of the leather (9) and for delivering a quality value characterizing the leather (9) in regard to its quality category, the testing device (10) comprises screening means (16) for examining the homogeneity of the leather (9) auf, which may screen at least portions (22, 23, 24, 27, 29) of the leather (9) and which are formed for delivering screening data (D) to analysis means (19), and wherein there are formed analysis means (19) for comparing the screening data (D) with feature data typical for hide injuries or inhomogeneities, respectively, of the leather (9) and for classifying determined hide injuries of examined portions (22, 23, 24, 27, 29) of the leather (9) and wherein there are formed display means (20) for display the categorized hide injuries or quality value, respectively, of the leather (9), preferably per portion (22, 23, 24, 27, 29) of the leather (9).

12 Claims, 3 Drawing Sheets

(51) Int. Cl.
　　*C14B 17/00*　　(2006.01)
　　*G01N 23/04*　　(2006.01)

(56) References Cited

FOREIGN PATENT DOCUMENTS

| DE | 4216469 | * | 11/1993 |
| FR | 2 864 668 | A1 | 7/2005 |
| JP | 2009 115468 | A | 5/2009 |
| KR | 2003 0080288 | A | 10/2003 |
| SU | 604404 | A1 | 4/1981 |
| WO | WO 03/076915 | A1 | 9/2003 |
| WO | WO 2008/144717 | A1 | 11/2008 |
| WO | WO 2008144717 | A1 * | 11/2008 |

* cited by examiner

DEVICE FOR DETERMINING THE QUALITY OF ORTHOGONALLY PRETENSIONED LEATHER

The invention relates to a testing device for determining the quality of leather in the production of leather, wherein the testing device is formed for examining the quality category of leather and for delivering a quality value characterizing the leather in regard to its quality category.

In the production of leather, there is produced, in a sequence of mechanical and chemical processes, a completed leather hide from the hide or skin of an animal. As leather is used in a variety of applications, the quality of the leather hide has to be determined before and after, respectively, the process steps of leather production, in order to define the type of use or application the leather hide or portions of the leather hide are suited for.

In the quality control of leather, there are used several different testing devices for examining different quality criteria. By means of a so-called Taber or Veslic or Martindale testing device, respectively, the abrasion resistance of the leather is inspected. By means of a so-called flexometer, the buckling resistance of the leather is examined. By means of a fire test the flammability of the leather is examined. The leather is exposed to light and UV radiation in order to test its light-fastness. By means of another device, there is performed a colour measurement of the colour of the leather surface. Furthermore, the leather is inspected on strength (for example, tensile strength, tear strength, elasticity). Finally, there is performed a manual and visual final control, wherein there is evaluated essentially the quality of the leather in regard to hide injuries as quality criterion.

In the case of calf leather, there are known many different types of hide injuries, which are the result of harms, lichens, mites, cracks, fork impacts or other causes. Every type of hide injury has its typical formation, with fork impacts having, for example, a small and round circumference and hide injuries due to fat wrinkles having longitudinal and parallel circumferences.

For the industrial production of leather, there were elaborated leather feature catalogues, wherein the individual types of hide injuries are defined as quality criterion and wherein, according to size, extent and depth of the hide injuries, hide injuries are allocated to objective quality values or quality classes, respectively. In the manual and visual final control, every leather hide is inspected for hide injuries, and a quality value is allocated to portions of the leather hide or also the entire leather hide.

It has proven as disadvantageous in the known procedures for quality control of leather that there may only be employed very skilled and experienced workers for the visual final control, who have already inspected many leather hides. Furthermore, the visual final control is very time consuming and hence remains a rather subjective decision, even though there have been defined objective evaluation criteria through the elaboration of the leather feature catalogues.

The invention hence aims at providing an objective quality control for leather, wherein there may be examined a great number of leather hides per tine unit in regard to their hide injuries.

The invention realizes this aim by providing the testing device with screening means for inspecting the homogeneity of the leather, wherein these screening means may screen at least portions of the leather and are formed for delivering screening data to analysis means, wherein the analysis means are formed for comparing screening data with feature data typical for hide injuries or inhomogeneities of the leather, respectively, and for categorizing the determined hide injuries of examined portions of the leather, and wherein the display means are formed for displaying the categorized hide injuries or quality value of the leather, respectively, preferably per portion of the leather.

This gives the advantage that the quality value determined for the leather hide by the testing device is a quality value that has been determined on the basis of objective criteria and by means of an objective testing procedure, hence making the quality of leather hides comparable for the very first time. It is especially preferable to allocate determined portions of the leather hide, which may be displayed by the display means, to determined quality values. These quality values may then, together with the pattern for the leather to be cut, for example for leather covers of steering wheels, be further processed, thereby guaranteeing an optimum use of the leather hide.

It is further preferably that the screening means are provided with an X-ray source screening the leather hides, as screening by use of X-rays enables for a rather cost-effective embodiment. But there may also be used other screening methods known from the medical field, such as for example magnetic resonance or computer tomography.

Tests have shown that hide injuries may be recognized more easily, if the leather is pretensioned; for this reason the provision of pretensioning means in the testing device will guarantee a better detectability of hide injuries.

It has proven as advantageous for reasons of costs and maintenance to form the screening means in the form of bars, inbetween which the leather will be clamped between the X-ray source and the X-ray detector. In a variant embodiment the testing device has leather transport means for transporting the leather through the bars, and in another embodiment the screening means are equipped with transport means in order to transport the screening means alongside the leather.

It is especially advantageous to configure the screening means sufficiently big so that the entire leather hide may be inspected in the course of one single inspection step.

As detectors may cause defective pixel, it has proved advantageous that the analysis means have a pre-processing step detecting such defective pixel and eliminating these before the further processing of the screening data. In this way, there are obtained essentially more precise quality values.

In the leather features catalogues, there are described the known types of hide injuries. It has proven advantageous to elaborate electronically processible feature data and store these in the analysis means, corresponding to the visual presentation of known types of hide injuries. In the analysis means there are further stored tolerance levels, in the range of which these feature data may fall. On the basis of these feature data and tolerance levels, the analysis means are formed for automatically identifying hide injuries by means of screening data of the leather hide. For a better identification and a further processing, the intensity values of the regions with hide injuries are amplified in the screening data, this even further improving quality control.

Further advantages of the invention are below described by means of an exemplary embodiment, with the invention, however, not being restricted to this exemplary embodiment.

FIG. 1 schematically shows a bovine, wherein the position of typical hide injuries is marked.

Figure 1:
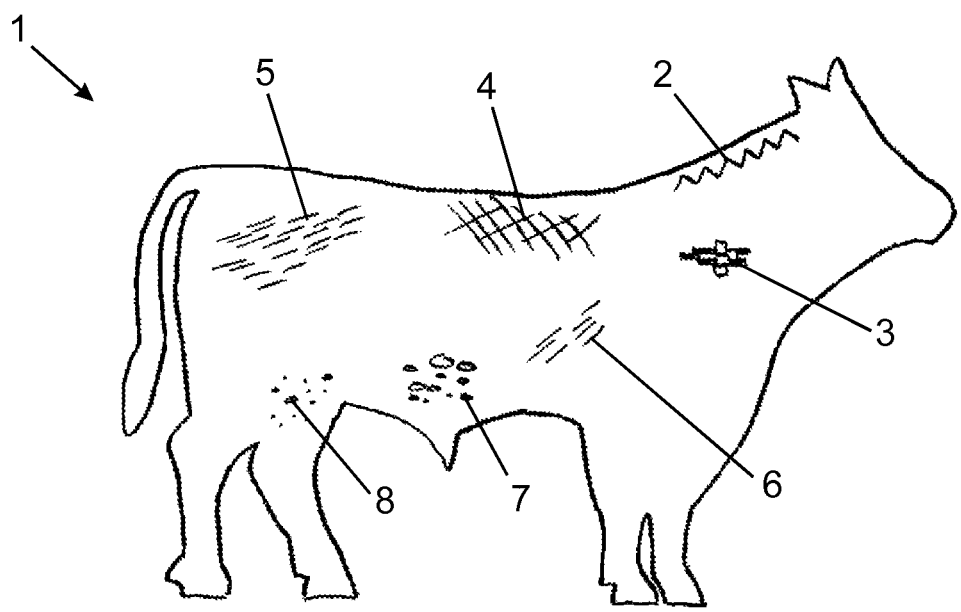

FIG. 1 schematically shows a bovine 1, wherein the position of typical hide injuries is marked. At the neck there are situated hide injuries 2 due to hedges or barbed wire and hide injuries 2 caused by mites. Lichens in the fur lead to hide injuries 4, dung to hide injuries 5, grooming damage to hide injuries 6, horn impacts to hide injuries 7 and driving accessories and fork marks to hide injuries 8.

This only constitutes a selection of hide injuries, which have been classified in so-called leather feature catalogues in regard to their form (extent, typical size, depth into the leather) and position.

Figure 2:
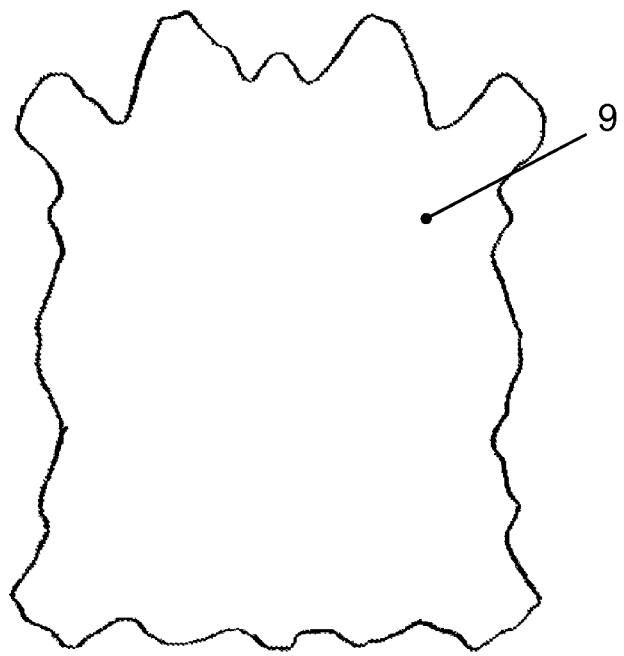
FIG. 2 shows a typical form of a bovine leather hide.

A leather hide 9 presented in FIG. 2 may be further processed for a variety of different uses and applications (leather sofa, leather coat, leather steering wheel, . . . ). Leather hides of different quality classes will be processed according to the type of use, of stress and load to be expected and price class of the final product. Portions of the leather hide 9 may have excellent quality, whereas other portions, for example due to hide injuries at the leather surface, may have a lower quality.

Figure 3:
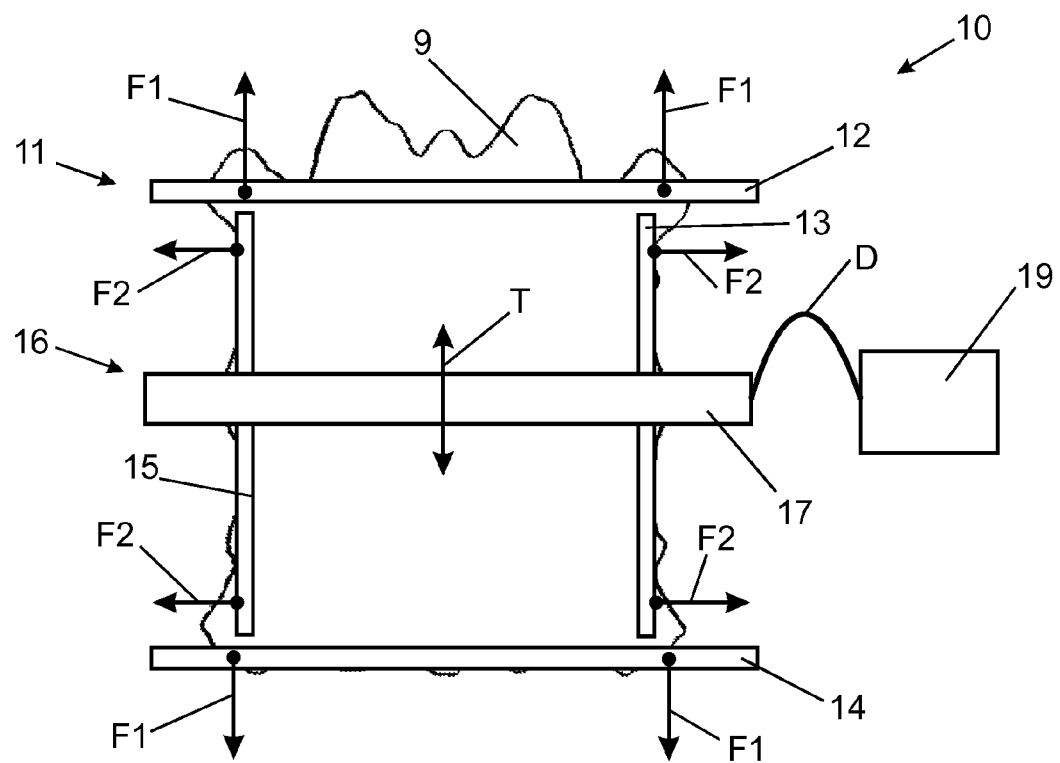
FIG. 3 shows a top view of a testing device for examining the quality of the clamped leather hide.

FIG. 3 schematically shows a top view of a testing device 10 for examining the quality of the clamped leather hide 9. The testing device 10 has pretensioning means 11, inbetween which the leather hide is clamped. The pretensioning means 11 have clamping bars 12, 13, 14 and 15, which act in FIG. 3, which is not further depicted, through the forces F1 and F2 onto the leather hide 9. By means of this pretensioning process, the leather hide is stretched by 1% to 10%, especially by 4% to 7%, in this way guaranteeing that the leather hide 9 is clamped evenly and may be easily screened.

Figure 4:
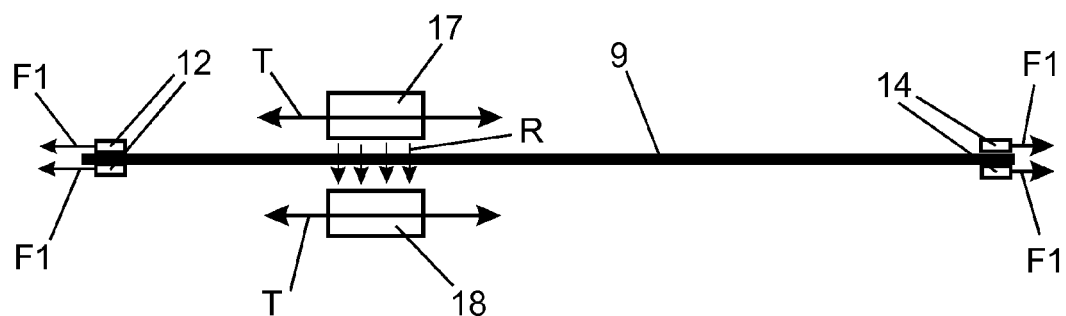
FIG. 4 shows a sectional view of the testing device according to FIG. 3.

The testing device 10 further comprises screening means 16 for examining the homogeneity of the leather hide 9 and which may screen more or less the entire leather hide 9. The screening means are formed by a bar-shaped X-ray source 17 and an X-ray detector 18, which is also bar-like depicted in FIG. 4. The X-ray source 17 transmits X-rays R to the X-ray detector 18, wherein the leather hide 9 situated there between is screened. A stepper motor, which is not shown in one of the figures, forms transport means for the screening means and is formed for synchronously transporting the X-ray source 17 and the X-ray detector 18 in the directions T. In a screening process, the stepper motor transports the X-ray source 17 and the X-ray detector 18 from the clamping bar 12 to the clamping bar 14, wherein the X-ray detector 18 delivers screening data D.

The testing device 10 further comprises analysis means formed by a computer 19. The screening data D obtained by the X-ray detector 18 are transferred together with the position data from the stepper motor to the computer 19. In this way, there may be allocated at determined points of time screening data D received by the computer 19 to determined portions of the leather hide 9.

The analysis means have a pre-processing step detecting defective pixel caused by the X-ray detector 18 and eliminating the defective pixel data in the screening data D before these are processed by the analysis means. The X-ray detector 18, for example, may have a defect at a certain position, and for this reason the screening data D obtained by this position of the X-ray detector will always have a maximum value. This maximum value is substituted by neighbouring screening data D in the pre-processing step. Those skilled in the art will know further procedures for eliminating defective pixel data, and therefore there will not be any further discussion herein of this topic.

In the computer 19 there is stored a data base of feature data of known types of hide injuries in cattle, which may be electronically processed. In these feature data there are, for example, stored screening data D which are typical for hide injuries due to fat wrinkles. Those skilled in the field of mathematics or gene analysis will know analysis methods, wherein certain data structures to be expected or data structures, which will deviate by predetermined tolerance levels from the expected data structures, may be found and identified in comprehensive data volumes. The computer 19 analyses the screening data D to identify feature data of determined hide injuries and displays its results for the user on a display 20 of the computer 19. It is advantageous to amplify the intensity values of the screening data D in the field of hide injuries.

Figure 5:
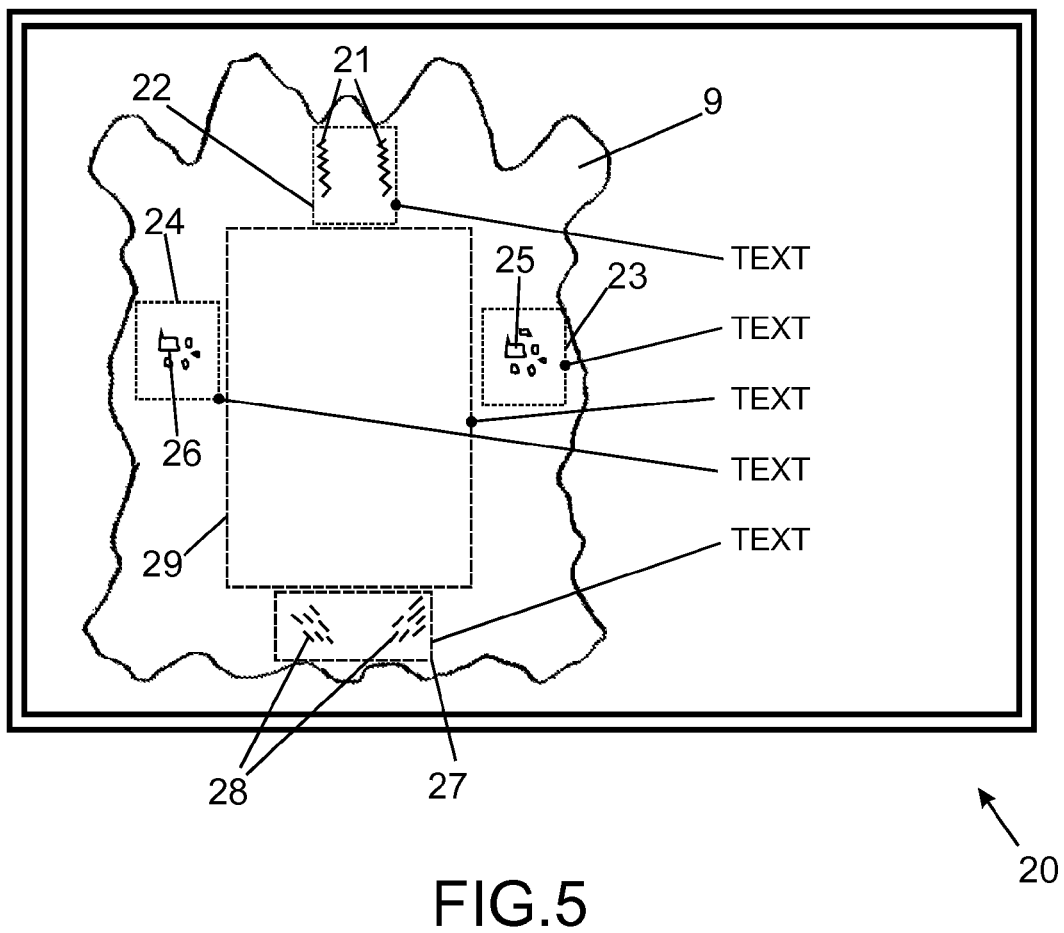
FIG. 5 shows display means of the testing device, which display the result of quality control.

FIG. 5 shows in an example what kind of information may be displayed on the display 20 of the computer 19. The contour of the leather hide 9 is displayed, wherein hide injuries, which have been detected by the screening means 16, and hide injuries, which have been assessed and evaluated by the analysis means of the computer, are marked. For example, there are indicated in the neck area of the leather hide 9 detected cracks 21, and a portion 22 of the leather hide 9 is marked. On the side of the computer display 20 there are presented in an explanatory text the quality value of the leather hide evaluated for this portion 22 as well as explanations on the type of hide injuries. Portions 23 and 24 of the leather hide 9 have hide injuries caused by horn impacts 25 and 26, and a portion 27 marks hide injuries on the basis of dung. A portion 29 indicates a portion of the leather hide 9 having a very high quality value without any essential hide injuries.

The portions of the leather hide 9 analyzed by the analysis means and displayed on the display 20 with different quality values may be used for planning the field of application and the pattern for the leather patches to be cut, in this way using the leather hide 9 in an optimum sort of way.

According to a further exemplary embodiment of the invention, the leather hide is clamped into the pretensioning devices, wherein the pretensioning devices form leather transport means driven by a stepper motor for transporting the leather during the testing step through the screening means. The advantage of this exemplary embodiment is that the screening means may be securely fixed and hence are less prone to errors.

There is to be noted that the examination of the quality of leather may also be realized independently of the proper production of leather by another company, and that the score of this patent is to be considered accordingly. A testing device according to the invention, in the majority of cases, will have display means for displaying the categorized hide injuries; it is, however, also possible that the corresponding data are not displayed but rather handed over together with the leather hide to the further processing company for cutting the leather hide.

It is to be noted that the screening means may also be formed as flat X-ray device and flat X-ray detector screening the entire leather hide without any transport means being necessary therefore. Furthermore, it is possible that the screening means, which have a rather small area, will screen the leather hide according to a predetermined screening scheme and in this way collect screening data of the entire leather hide.

It is to be noted that the testing device according to the invention may also be used for examining the quality of leather hides originating from pigs or other animals.

The invention claimed is:

1. A testing device for determining the quality of a leather hide, the testing device examining a quality category of the leather and delivering a quality value characterizing the leather in regard to its quality category, comprising:
   a pretensioner that pretensions or stretches at least a portion of the leather with substantially orthogonal forces;
   a screen for examining the homogeneity of the pretensioned or stretched portion of the leather and delivering screening data to an analyzer;
   the analyzer comparing the screening data with a database of feature data typical for hide injuries or inhomogeneities of leather and classifying determined hide injuries of the examined portions of the leather; and
   a display that displays the categorized hide injuries or quality value per screened portion of the leather.

2. The testing device according to claim 1, wherein the pretensioner comprises substantially orthogonal clamping bars providing said substantially orthogonal forces to the screened leather portion.

3. The testing device according to claim 2, wherein the pretensioner stretches the leather by 1% to 10%.

4. The testing device according to claim 2, wherein the pretensioner stretches the leather by 4% to 7%.

5. The testing device according to claim 1, 2, 3 or 4, wherein the screen comprises an X-ray source and an X-ray detector that detects the intensity of the X-rays weakened by the leather.

6. The testing device according to claim 1, 2, 3 or 4, further comprising a leather transport for transporting the leather through the screen during the testing process.

7. The testing device according to claim 1, 2, 3 or 4, further comprising a transport for transporting the screen alongside the pretensioned leather portion.

8. The testing device according to claim 1, wherein the screen examines the homogeneity of the entire leather hide.

9. The testing device according to claim 5, wherein the analyser detects a defective pixel in the X-ray detector and eliminates defective pixel data in the screening data before processing by the analyzer.

10. The testing device according to claim 1, 2, 3 or 4, wherein the analyser detects data in the screening data characterizing predetermined defects and increases their intensity values compared to the other screening data.

11. A method for producing leather hides, comprising the step of performing an examination of a stretched portion of leather hide using a testing device according to claim 1, 2, 3 or 4.

12. The testing device according to claim 10, wherein said predetermined defects are round, longitudinal or oval structures.

* * * * *

UNITED STATES PATENT AND TRADEMARK OFFICE
CERTIFICATE OF CORRECTION

PATENT NO. : 9,008,266 B2
APPLICATION NO. : 13/522694
DATED : April 14, 2015
INVENTOR(S) : Georg Kraus-Guentner It is certified that error appears in the above-identified patent and that said Letters Patent is hereby corrected as shown below:

Title Page

(73) Assignee:
"Wollsdorp Leder Schmidt & Co. Ges.m.b.H, Weiz (AT)" should read
-- Wollsdorf Leder Schmidt & Co. Ges.m.b.H, Weiz (AT) --.

(57) ABSTRACT:
Line 7, "auf," should be deleted.

(56) FOREIGN PATENT DOCUMENTS, Page 2:
"DE    4 216 469 * 11/1993" should be deleted;
"WO    WO 2008144717 A1* 11/2008" should be deleted;
"JP    2009 115468 A 5/2009" should read -- JP 2009-115468 A 5/2009 --; and
"SU    604404 A1 4/1981" should read -- RU 604404 A1 4/1981 --.

In the Specification

COLUMN 2:
Line 17, "preferably" should read -- preferable --.

COLUMN 3:
Line 29, "especially" should read -- preferably --.

Signed and Sealed this
Twenty-seventh Day of October, 2015

Michelle K. Lee
*Director of the United States Patent and Trademark Office*